(12) United States Patent
Stigall et al.

(10) Patent No.: US 11,311,271 B2
(45) Date of Patent: Apr. 26, 2022

(54) CATHETER WITH INTEGRATED CONTROLLER FOR IMAGING AND PRESSURE SENSING

(71) Applicant: Koninklijke Philips N.V, Amsterdam (NL)

(72) Inventors: Jeremy Stigall, Carlsbad, CA (US); Joseph Lauinger, San Diego, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 952 days.

(21) Appl. No.: 14/692,511

(22) Filed: Apr. 21, 2015

(65) Prior Publication Data

US 2015/0305708 A1    Oct. 29, 2015

Related U.S. Application Data (60) Provisional application No. 61/983,101, filed on Apr. 23, 2014.

(51) Int. Cl.
*A61B 8/12* (2006.01)
*A61B 5/0215* (2006.01)
(Continued)

(52) U.S. Cl.
CPC ............ *A61B 8/12* (2013.01); *A61B 5/02007* (2013.01); *A61B 5/0215* (2013.01); *A61B 8/4461* (2013.01);
(Continued)

(58) Field of Classification Search
CPC .. A61B 8/12; A61B 8/445; A61B 8/56; A61B 5/02007; A61B 5/0215
See application file for complete search history.

(56) References Cited

U.S. PATENT DOCUMENTS

| | | | |
|---|---|---|---|
| 4,917,097 A | * | 4/1990 | Proudian .................. A61B 8/12 600/463 |
| 5,243,988 A | | 9/1993 | Sieben |

(Continued)

FOREIGN PATENT DOCUMENTS

| | | |
|---|---|---|
| JP | 2011209051 A | 10/2011 |
| WO | 1996007351 A1 | 3/1996 |

OTHER PUBLICATIONS

Universal Serial Bus Specification, Revision 2.0, released Apr. 27, 2000, pp. 17-19.*
(Continued)

*Primary Examiner* — Colin T. Sakamoto (57) ABSTRACT

An intravascular ultrasound (IVUS) device that includes a flexible elongate member having a proximal portion and a distal portion; a controller coupled to the distal portion of the flexible elongate member; an ultrasound transducer disposed at the distal portion of the flexible elongate member and in communication with the controller; a pressure transducer disposed at the distal portion of the flexible elongate member and in communication with the controller; and plurality of conductors extending from the controller to the proximal portion of the catheter, at least one conductor of the plurality of conductors being configured to carry both the signals representing information captured by the ultrasound transducer and information captured by the pressure transducer.

20 Claims, 6 Drawing Sheets

(51) Int. Cl.
*A61B 5/02* (2006.01)
*A61B 8/00* (2006.01)

(52) U.S. Cl.
CPC .............. *A61B 8/463* (2013.01); *A61B 8/54* (2013.01); *A61B 8/56* (2013.01); *A61B 2562/028* (2013.01); *A61B 2562/12* (2013.01); *A61B 2562/221* (2013.01)

(56) References Cited

U.S. PATENT DOCUMENTS

| | | | |
|---|---|---|---|
| 5,546,948 A | 8/1996 | Hamm | |
| 5,715,827 A | 2/1998 | Corl | |
| 5,857,974 A * | 1/1999 | Eberle | A61B 1/0011 29/25.35 |
| 6,641,540 B2 | 11/2003 | Fleischman | |
| 8,104,479 B2 | 1/2012 | Glynn | |
| 8,277,386 B2 | 10/2012 | Ahmed et al. | |
| 8,298,156 B2 | 10/2012 | Manstrom | |
| 8,485,985 B2 | 7/2013 | Manstrom | |
| 2003/0018273 A1* | 1/2003 | Corl | G01L 19/149 600/486 |
| 2004/0230131 A1 | 11/2004 | Kassab et al. | |
| 2009/0171201 A1 | 7/2009 | Olson | |
| 2010/0262014 A1 | 10/2010 | Huang | |
| 2011/0224552 A1* | 9/2011 | Poland | A61B 8/00 600/459 |
| 2013/0131523 A1 | 5/2013 | Suchecki | |
| 2013/0303907 A1 | 11/2013 | Corl | |
| 2013/0303914 A1 | 11/2013 | Hiltner | |
| 2013/0303919 A1* | 11/2013 | Corl | A61B 8/4494 600/467 |
| 2013/0303920 A1 | 11/2013 | Corl | |
| 2013/0331831 A1 | 12/2013 | Werneth et al. | |
| 2014/0005521 A1 | 1/2014 | Khler et al. | |
| 2014/0081244 A1 | 3/2014 | Voeller et al. | |
| 2014/0180032 A1* | 6/2014 | Millett | A61B 8/4416 600/301 |
| 2014/0180072 A1* | 6/2014 | Davies | G01S 7/52074 600/424 |
| 2014/0187960 A1 | 7/2014 | Corl | |

OTHER PUBLICATIONS

Da Franca "Analog-to-Digital Conversion" Wiley Encyclopedia of Electrical and Electronics Engineering 1999 (Year: 1999).*
Korean Intellectual Property Office, International Search Report for PCT/US2015/026757 dated Jul. 15, 2015, 15 pages.

* cited by examiner

CATHETER WITH INTEGRATED CONTROLLER FOR IMAGING AND PRESSURE SENSING

The present application claims priority to and the benefit of the U.S. Provisional Patent Application Nos. 61/983,101, filed Apr. 23, 2014, which is hereby incorporated by reference in its entirety.

TECHNICAL FIELD

The present disclosure relates generally to systems, devices, and methods employing a controller for both imaging and pressure sensors for diagnostically assessing a target region of a patient. More particularly, the present disclosure relates to systems, devices, and methods that utilize a common controller to perform intravascular ultrasound (IVUS) imaging and pressure sensing for diagnostically assessing a target region of a patient, such as a patient's vasculature, for example.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. IVUS imaging uses ultrasound echoes to form a cross-sectional image of the vessel of interest. Typically, the ultrasound transducer on an IVUS catheter both emits ultrasound pulses and receives the reflected ultrasound echoes. The ultrasound waves pass easily through most tissues and blood, but they are partially reflected by discontinuities arising from tissue structures (such as the various layers of the vessel wall), red blood cells, and other features of interest. The IVUS imaging system, which is connected to the IVUS catheter by way of a patient interface module, processes the received ultrasound echoes to produce a cross-sectional image of the vessel where the catheter is located.

There are two types of IVUS catheters in common use today: solid-state and rotational, with each having advantages and disadvantages. Solid-state IVUS catheters use an array of ultrasound transducers (typically 64) distributed around the circumference of the catheter and connected to an electronic multiplexer circuit. The multiplexer circuit selects array elements for transmitting an ultrasound pulse and receiving the echo signal. By stepping through a sequence of transmit-receive pairs, the solid-state IVUS system can synthesize the effect of a mechanically scanned transducer element, but without moving parts. Since there is no rotating mechanical element, the transducer array can be placed in direct contact with the blood and vessel tissue with minimal risk of vessel trauma and the solid-state scanner can be wired directly to the imaging system with a simple electrical cable and a standard detachable electrical connector.

In the typical rotational IVUS catheter, a single ultrasound transducer element fabricated from a piezoelectric ceramic material is located at the tip of a flexible driveshaft that spins inside a plastic sheath inserted into the vessel of interest. The transducer element is oriented such that the ultrasound beam propagates generally perpendicular to the axis of the catheter. The fluid-filled sheath protects the vessel tissue from the spinning transducer and driveshaft while permitting ultrasound signals to freely propagate from the transducer into the tissue and back. As the driveshaft rotates (typically at 30 revolutions per second), the transducer is periodically excited with a high voltage pulse to emit a short burst of ultrasound. The same transducer then listens for the returning echoes reflected from various tissue structures, and the IVUS imaging system assembles a two dimensional display of the vessel cross-section from a sequence of several hundred of these ultrasound pulse/echo acquisition sequences occurring during a single revolution of the transducer.

While the solid-state IVUS catheter is simple to use, thanks to its lack of moving parts, it cannot match the image quality available from a rotational IVUS catheter. It is difficult to operate a solid-state IVUS catheter at the same high frequency as a rotational IVUS device, and the lower operating frequency of solid-state IVUS catheters translates into poorer resolution compared to that of a higher frequency rotational IVUS catheter. There are also artifacts such as sidelobes, grating lobes, and poor elevation focus (perpendicular to the imaging plane) that arise from the array-based imaging that are greatly reduced or completely absent with a rotational IVUS device. Despite the image quality advantages of the rotational IVUS catheter, each of these devices has found a niche in the interventional cardiology market, with solid-state IVUS preferred in circumstances where ease-of-use is paramount and the reduced image quality is acceptable for the particular diagnostic needs, while rotational IVUS is preferred where image quality is paramount and the more time-consuming catheter preparation is justified.

In the rotational IVUS catheter, the ultrasound transducer is typically a piezoelectric ceramic element with low electrical impedance capable of directly driving an electrical cable connecting the transducer to the imaging system hardware. In this case, a single pair of electrical leads (or coaxial cable) is used to carry the transmit pulse from the system to the transducer and to carry the received echo signals from the transducer back to the imaging system by way of a patient interface module, where they are assembled into an image.

Some catheters utilize pressure sensors disposed to assess the severity of a stenosis in a blood vessel, including ischemia-causing lesions. One method for assessing the severity of a stenosis includes taking two blood pressure measurements with the pressure sensor: one measurement distal or downstream to the stenosis and one measurement proximal or upstream to the stenosis. The differences in pressure may be used to calculate a value indicating the severity of the stenosis. Common treatment options include angioplasty, atherectomy, and stenting.

While existing IVUS catheters and existing pressure sensing catheters deliver useful diagnostic information, there is a need for combined pressure sensing and IVUS catheters that enable a health care provider to efficiently perform diagnostic assessment of multiple ways, such as imaging and pressure sensing while requiring only a single catheter to be introduced to a patient. There is also a need for combined pressure sensing and IVUS catheters that are integrated together in a manner that effectively and efficiently conserves space or volume required so that the catheter is still sized small enough to access small target areas.

Accordingly, there remains a need for improved devices, systems, and methods for providing a compact and efficient catheter that has both ultrasound transducers for imaging or determining physical dimensions and a pressure sensor for measuring the pressure of fluid within a blood vessel.

The present disclosure addresses one or more of the shortcomings in the prior art.

SUMMARY

Embodiments of the present disclosure provide a compact and efficient circuit architecture and electrical interface to a polymer piezoelectric micro-machined ultrasonic transducer used in an intravascular ultrasound system.

In an exemplary aspect, the present disclosure is directed to an intravascular ultrasound (IVUS) device that includes a flexible elongate member having a proximal portion and a distal portion; a controller coupled to the distal portion of the flexible elongate member; an ultrasound transducer disposed at the distal portion of the flexible elongate member and in communication with the controller; a pressure transducer disposed at the distal portion of the flexible elongate member and in communication with the controller; and a plurality of conductors extending from the controller to the proximal portion of the catheter, at least one conductor of the plurality of conductors being configured to carry both the signals representing information captured by the ultrasound transducer and information captured by the pressure transducer.

In an aspect, the ultrasound transducer comprises an ultrasound transducer imaging element configured to be rotated about an axis of the elongate member. In an aspect, the ultrasound transducer comprises a transducer array formed of a plurality of ultrasound transducers. In an aspect, the plurality of conductors comprises a four-lead electrical cable and the controller is configured to communicate signals based on information from both the ultrasound transducer and the pressure transducer on the same wire. In an aspect, the pressure transducer connects to the controller via three leads. In an aspect, a distal portion of the four-lead electrical cable is electrically coupled to the controller. In an aspect, a proximal portion of the four-lead electrical cable is coupled to a connector configured to connect the four-lead electrical cable to a patient interface module (PIM). In an aspect, the controller is disposed adjacent the ultrasound transducer. In an aspect, the pressure transducer is disposed distal of the ultrasound transducer. In an aspect, the flexible elongate member comprises a guidewire lumen for receiving a guidewire.

In an exemplary aspect, the present disclosure is directed to an intravascular ultrasound (IVUS) imaging and pressure sensing system, comprising a catheter and a user interface. The catheter includes a controller disposed at a distal portion of the catheter; an ultrasound transducer disposed at the distal portion of the catheter and in communication with the controller; a pressure transducer disposed at the distal portion of the catheter and in communication with the controller; and a plurality of conductors extending from the controller toward the proximal portion of the catheter, at least one conductor of the plurality of conductors being configured to carry signals representing both information captured by the ultrasound transducer and information captured by the pressure transducer. The user interface is in communication with the catheter and configured to present information based on the signals carried by the plurality of conductors.

In an aspect, the ultrasound transducer comprises an ultrasound transducer imaging element configured to be rotated about an axis of the elongate member. In an aspect, the ultrasound transducer comprises a transducer array formed of a plurality of ultrasound transducers. In an aspect, the cable is a four-lead electrical cable and the controller is configured to communicate signals based on information from both the ultrasound transducer and the pressure transducer on the same wire. In an aspect, the pressure transducer connects to the controller via three leads. In an aspect, a distal portion of the four-lead electrical cable is electrically coupled to the controller. In an aspect, a proximal portion of the four-lead electrical cable is coupled to a connector configured to connect the four-lead electrical cable to a patient interface module (PIM).

In an exemplary aspect, the present disclosure is directed to a method of assessing a patient comprising: receiving information captured by an ultrasound transducer disposed at a distal portion of a catheter; receiving information captured by a pressure transducer disposed at a distal portion of the catheter; generating communication signals representing the information from the ultrasound transducer and from the pressure transducer at a controller carried on the catheter; and transmitting the communication signals representing both the information captured by the ultrasound transducer and information captured by the pressure transducer from a controller carried on the catheter to a user interface.

In an aspect, receiving information captured by an ultrasound transducer and receiving information captured by a pressure transducer are performed simultaneously. In an aspect, transmitting the communication signals representing both the information captured by the ultrasound transducer and information captured by the pressure transducer comprises transmitting signals in real time as they are received from the ultrasound transducer and the pressure transducer. In an aspect, the generating includes converting analog signals received from one of the pressure transducer and ultrasound transducer into digital signals prior to the transmitting.

Some embodiments of the present disclosure establish a circuit architecture that provides the needed signal amplification and an efficient pulser circuit, with an electrical interface that requires a small number of electrical leads. In that regard, a smaller number of leads allows larger diameter conductors to be used within the limited space of the flexible elongate member, resulting in reduced cable attenuation and low electrical loss in the interconnect cable extending along the length of the flexible elongate member. Further, embodiments of the present disclosure provide excellent cable impedance matching. In that regard, a four-lead interface facilitates a cable design consisting of a pair of balanced transmission lines, with each transmission line properly terminated to minimize reflections and distortion of the frequency response that can cause artifacts or degradation in the image. Alternatively, a four-lead interface facilitates an alternative cable design (shielded twisted triplet) consisting of a one balanced transmission line, properly terminated to minimize reflections and distortion of the frequency response that can cause artifacts or degradation in the image, while the high voltage DC and ground signals are carried by an unbalanced conductor pair, where impedance matching and balance are not important.

Further, embodiments of the present disclosure also provide low signal coupling. For example, the four-lead cable can be operated in a "star quad" configuration with diagonal conductor pairs forming independent transmission lines. In this configuration, coupling between diagonal signal pairs, each operated in differential mode, is minimized by the symmetry of the coupling to provide low cross-talk between the multiple signals carried by the cable. Also, a shielded twisted triplet cable can be operated in a configuration with two of the three twisted conductors forming a balanced transmission line, while the third twisted conductor and the shield carry the high voltage DC and ground signals. In this configuration, coupling between the balanced signal pair operated in differential mode and the other conductors is minimized by symmetry.

Further still, embodiments of the present disclosure provide low electromagnetic interference (EMI). In that regard, the four-lead interface facilitates a cable design consisting of a pair of balanced transmission lines. The balanced design inhibits radiation of EMI, as well as reduces the susceptibility of the system to external interference from other devices. The four-lead interface cable is jacketed with an electrical shield conductor in some instances to further suppress EMI and susceptibility to external interference. Also, a four-lead interface facilitates a cable design consisting of a shielded twisted triplet, comprised of one balanced signal pair and one unbalanced pair. This balanced design inhibits radiation of EMI, as well as reduces the susceptibility to external interference from other devices, while the unbalanced pair carries only low frequency signals, not prone to generating EMI. The shielded twisted triplet cable design includes an electrical shield conductor to further suppress EMI and susceptibility to external interference.

Embodiments of the present disclosure also provide design flexibility, small integrated circuit die dimensions suitable for use in intravascular catheters and/or guidewires, low power dissipation, high transmit voltages, and an efficient protection circuit. For example, the use of a serial communication scheme makes it feasible to add flexibility and advanced features to the circuit design without complicating the four-lead physical interface between the PIM and the transducer. The circuit described herein is implemented in a compact application-specific integrated circuit (ASIC or controller as used herein) and the four lead electrical interface consumes only a small portion of the device area such that the system can be implemented in catheters and guidewires having an outer diameter as small as 0.020" (0.5 mm) in some embodiments. Embodiments of the circuits described herein are designed to minimize power dissipation to avoid excessive temperature rise at the distal end of the catheter. Also, embodiments of the circuits described herein include a high voltage pulser at the distal end of the catheter that avoids the significant cable losses associated with a PIM-based pulser circuit. This approach also reduces the EMI that might otherwise be produced by sending a high voltage transmit pulse through the electrical cable extending along the length of the device, connecting the PIM to the transducer. Further, embodiments of the circuits described herein implement an efficient protection circuit using an actively controlled analog switch to isolate the sensitive amplifier inputs from the high voltage transmit pulse applied to the transducer. This analog switch based protection circuit design is facilitated by the proximity between the transmitter, amplifier, protection, and timing circuits, all of which are integrated into a single controller.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

The systems, devices, and methods disclosed herein relate to a system capable of carrying out both imaging using an ultrasound transducer and pressure sensing using a pressure transducer. As described herein, the ultrasound transducer and the pressure transducer share a common conventional cable and other electrical components. With fewer components extending the length of the catheter, the overall diameter of the catheter may be smaller than could otherwise be achieved. In addition, some manufacturing steps may be eliminated when compared to manufacturing with distinct IVUS imaging and pressure transducers.

Figure 1:
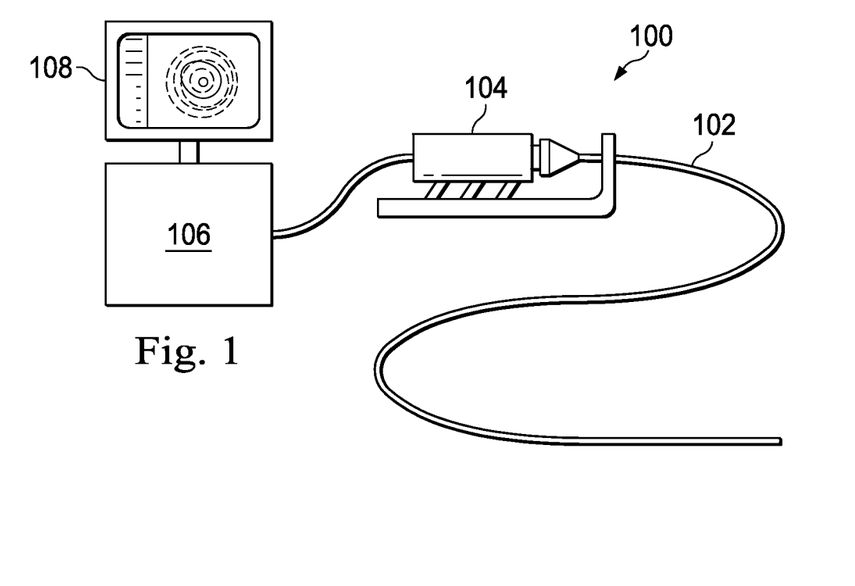
FIG. 1 is a diagrammatic schematic view of an imaging system according to an embodiment of the present disclosure.

Referring to FIG. 1, shown therein is an IVUS imaging and pressure sensing system 100 according to an embodiment of the present disclosure. In some embodiments of the present disclosure, the IVUS imaging and pressure sensing system 100 is a piezoelectric micromachined ultrasound transducer (PMUT) rotational IVUS imaging and pressure sensing system. In that regard, the main components of the IVUS imaging and pressure sensing system 100 are an IVUS and pressure sensing catheter 102, a PMUT catheter compatible patient interface module (PIM) 104, an IVUS and pressure console or processing system 106, and a monitor 108 to display the IVUS images and any pressure information or data generated by the IVUS and pressure console 106.

At a high level, the IVUS and pressure sensing catheter 102 emits ultrasonic energy from an IVUS transducer at the tip of the catheter. The ultrasonic energy is reflected by tissue structures surrounding the IVUS transducer and the echo signals from the tissue are received and amplified by the IVUS transducer. The IVUS and pressure sensing catheter 102 also detects data indicative of pressure within a target region of the patient with a pressure transducer at the tip of the device. While emitting ultrasonic energy and receiving echoes, or at intermittent intervals, the IVUS and pressure sensing catheter 102 takes pressure readings within the target body region, often within the vasculature of a patient. As described herein, the IVUS transducer and the pressure transducer share an ASIC controller and the same communication and power cable extending toward the proximal end of the IVUS and pressure sensing catheter.

The PIM 104 facilitates communication of signals between the IVUS and pressure console 106 and the IVUS and pressure sensing catheter 102 to control the operation of the IVUS transducer and the pressure transducer. Controlling the operation of the IVUS transducer includes generating control signals to configure the IVUS transducer and trigger the transmitter circuit and transfer echo signals captured by the IVUS transducer to the IVUS and pressure console 106. With regard to the echo signals, the PIM 104 forwards the received signals and, in some embodiments, performs preliminary signal processing prior to transmitting the signals to the console 106. In examples of such embodiments, the PIM 104 performs amplification, filtering, and/or aggregating of the data. In an embodiment, the PIM 104 also supplies high- and low-voltage DC power to support operation of the circuitry within the IVUS transducer, as well as the pressure sensor. At the same time, the PIM 104 forwards pressure data received from the pressure transducer and, in some embodiments, performs preliminary signal processing prior to transmitting the pressure data to the console 106. In examples of such embodiments, the PIM 104 performs amplification, filtering, and/or aggregating of the pressure data.

The IVUS and pressure console 106 receives the echo data from the IVUS transducer and receives pressure data from the pressure transducer by way of the PIM 104 and processes the data to create an image of the tissue surrounding the IVUS transducer and assesses the pressure within the target region. In some instances, the IVUS and pressure console 106 is configured to calculate a fractional flow reserve (FFR) based on the obtained pressure measurements. The console 106 may also display the image and/or pressure information, including the FFR on the monitor 108.

FFR is a currently accepted technique for assessing the severity of a stenosis in a blood vessel, including ischemia-causing lesions. It is defined as the ratio of the maximal blood flow in a stenotic artery, taken distal to the lesion, to normal maximal flow. Accordingly, to calculate the FFR for a given stenosis, two blood pressure measurements are taken: one measurement distal or downstream to the stenosis and one measurement proximal or upstream to the stenosis. FFR is a calculation of the ratio of the distal pressure measurement relative to the proximal pressure measurement. FFR provides an index of stenosis severity that allows determination as to whether the blockage limits blood flow within the vessel to an extent that treatment is required. The more restrictive the stenosis, the greater the pressure drop across the stenosis, and the lower the resulting FFR. FFR measurements can be used as a decision point for guiding treatment decisions. The normal value of FFR in a healthy vessel is 1.00, while values less than about 0.80 are generally deemed significant and require treatment. Common treatment options include angioplasty, atherectomy, and stenting.

As discussed in greater detail below, the IVUS and pressure sensing catheter 102 includes a PMUT ultrasound transducer along with its associated circuitry mounted near a distal tip of the catheter, a four conductor electrical cable, and the appropriate electrical connector to support the rotational interface. The IVUS and pressure sensing catheter 102 also detects data indicative of pressure within a target region of the patient with a pressure transducer near the distal tip of the catheter.

The PIM 104 generates the required sequence of transmit trigger signals and control waveforms to regulate the operation of the circuit and processes the amplified echo signals received over that same conductor pair. The PIM 104 also supplies the high- and low-voltage DC power supplies to support operation of the IVUS and pressure sensing catheter 102. An important feature of the PIM 104 is that it must deliver DC supply voltages to the PMUT circuitry of the catheter 102 across a rotational interface. This requirement largely precludes the option of a rotary transformer, commonly used for traditional rotational IVUS systems, since a transformer can only convey AC signals from the primary to the secondary side. Practical options for delivering DC power across a rotating interface include the use of slip-rings and/or the implementation of the active spinner technology described in U.S. Patent Application Publication No. 2010/0234736, which is hereby incorporated by reference in its entirety.

Figure 2:
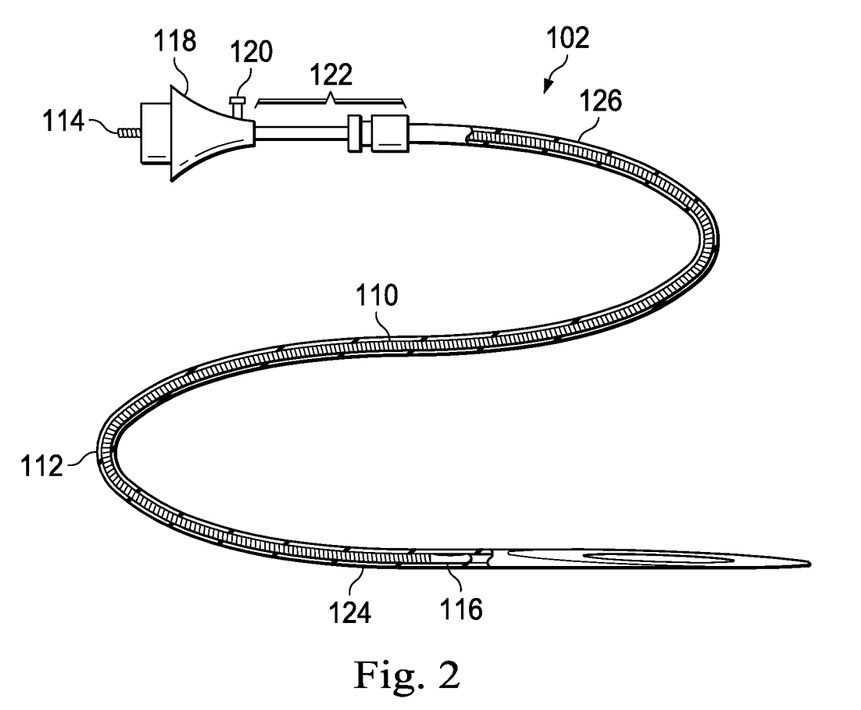
FIG. 2 is a diagrammatic, partial cutaway perspective view of an imaging device according to an embodiment of the present disclosure.

Referring now to FIG. 2, shown therein is a diagrammatic, partial cutaway perspective view of the rotational IVUS and pressure sensing catheter 102 according to an embodiment of the present disclosure. In that regard, FIG. 2 shows additional detail regarding the construction of the IVUS and pressure sensing catheter 102. In some respects, this catheter is similar to traditional rotational IVUS catheters, such as the Revolution® catheter available from Volcano Corporation and described in U.S. Pat. No. 8,104,479, or those disclosed in U.S. Pat. Nos. 5,243,988 and 5,546,948, each of which is hereby incorporated by reference in its entirety. In that regard, the IVUS and pressure sensing catheter 102 includes an imaging core 110 and an outer catheter/sheath assembly 112. The imaging core 110 includes a flexible drive shaft that is terminated at the proximal end by a rotational interface 114 providing electrical and mechanical coupling to the PIM 104 of FIG. 1. The distal end of the flexible drive shaft of the imaging core 110 is coupled to a transducer housing 116 containing the PMUT and associated circuitry, which are described in greater detail below. The catheter/sheath assembly 112 includes a hub 118 that supports the rotational interface and provides a bearing surface and a fluid seal between the rotating and non-rotating elements of the catheter assembly. The hub 118 includes a luer lock flush port 120 through which saline is injected to flush out the air and fill the inner lumen of the sheath with an ultrasound-compatible fluid at the time of use of the catheter. The saline or other similar flush is typically required since air does not readily conduct ultrasound. Saline also provides a biocompatible lubricant for the rotating driveshaft. The hub 118 is coupled to a telescope 122 that includes nested tubular elements and a sliding fluid seal that permit the catheter/sheath assembly 112 to be lengthened or shortened to facilitate axial movement of the transducer housing within an acoustically transparent window 124 of the distal portion of the catheter 102. In some embodiments, the window 124 is composed of thin-walled plastic tubing fabricated from material(s) that readily conduct ultrasound waves between the transducer and the vessel tissue with minimal attenuation, reflection, or refraction. A proximal shaft 126 of the catheter/sheath assembly 112 bridges the segment between the telescope 122 and the window 124, and is composed of a material or composite that provides a lubricious internal lumen and optimum stiffness, but without the need to conduct ultrasound.

Figure 3:
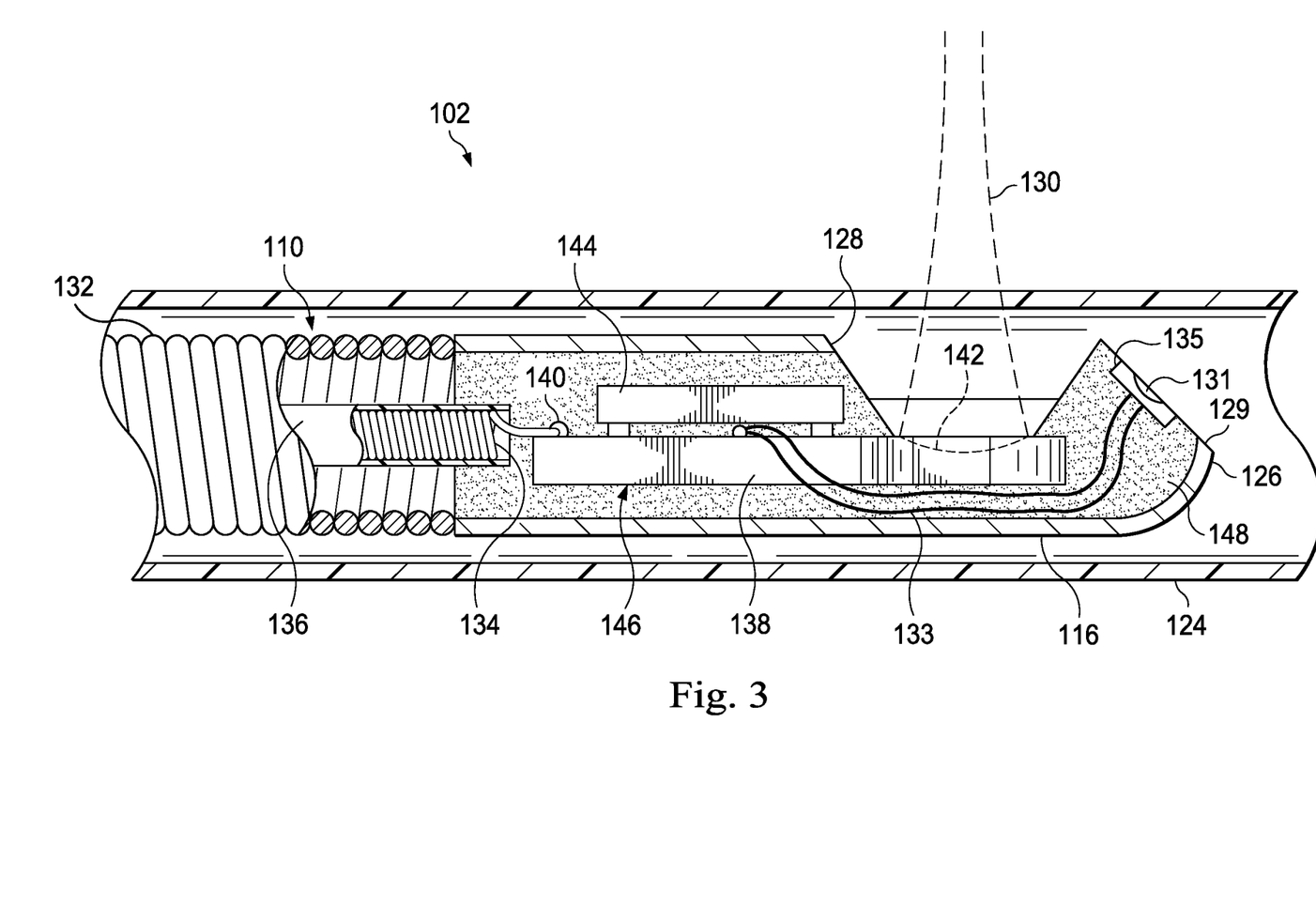
FIG. 3 is a diagrammatic, cross-sectional side view of a distal portion of the imaging device of FIG. 2.

Referring now to FIG. 3, shown therein is a cross-sectional side view of a distal portion of the catheter 102 according to an embodiment of the present disclosure. In particular, FIG. 3 shows an expanded view of aspects of the distal portion of the imaging core 110. In this exemplary embodiment, the imaging core 110 is terminated at its distal tip by a housing 116 fabricated from stainless steel and provided with a rounded nose portion 126 and an imaging cutout 128 for the ultrasound beam 130 to emerge from the housing 116 and a pressure sensing cutout 129 for the pressure transducer 131 to detect pressure within the target anatomy.

In some embodiments, the flexible driveshaft 132 of the imaging core 110 is composed of two or more layers of counter wound stainless steel wires, welded, or otherwise secured to the housing 116 such that rotation of the flexible driveshaft also imparts rotation on the housing 116. In the illustrated embodiment, the PMUT MEMS 138 includes a spherically focused transducer 142 and carries an application-specific integrated circuit (ASIC) 144, also referenced herein as a controller.

The controller 144 is electrically coupled to the PMUT MEMS 138 through two or more connections. In that regard, in some embodiments of the present disclosure the controller 144 includes an amplifier, a transmitter, and a protection circuit associated with the PMUT MEMS. In some embodiments, the controller 144 is flip-chip mounted to the substrate of the PMUT MEMS 138 using anisotropic conductive adhesive or suitable alternative chip-to-chip bonding method. When assembled together the PMUT MEMS 138 and the controller 144 form a controller/MEMS hybrid assembly 146 that is mounted within the housing 116.

An electrical cable 134 with optional shield 136 is attached to the controller/MEMS hybrid assembly 146 with solder 140. The electrical cable 134 extends through an inner lumen of the flexible driveshaft 132 to the proximal end of the imaging core 110 where it is terminated to the electrical connector portion of the rotational interface 114 shown in FIG. 2.

Embodiments of the present disclosure identify a four wire electrical interface that offers a wide array of benefits, with minimal compromise to the performance of the circuit and transducer, while maintaining a small cable dimension that can be readily accommodated by a rotational IVUS catheter. One implementation of such an arrangement for the electrical cable uses four electrical conductors, twisted together into a symmetrical quad and treated as two diagonal conductor pairs. In fact, a twisted quad occupies only a slightly larger cylindrical space (20% larger diameter) compared to a twisted pair of the same size conductors.

In such a twisted quad cable embodiment, one diagonal pair of conductors provides a balanced transmission line that serves the following multiple purposes: (1) conducting the balanced signal, such as data or information signals from the IVUS transducer and pressure transducer, from the controller amplifier output to the PIM amplifier input, (2) carrying the transmit trigger pulses as a balanced differential signal from the PIM transmit trigger circuitry to the transmitter and timing circuitry included on the controller, (3) supplying low voltage DC power as the common mode voltage on the conductor pair (referenced to the ground conductor of the second pair), (4) providing receiver timing signals to turn the amplifier circuitry on and off as needed to minimize power dissipation in the controller, and (5) creating a serial communication channel to support advanced features such as programmability. The second diagonal pair of conductors carries the high voltage supply and ground. The high voltage/ground pair, besides simply providing those DC voltages, also contributes a significant distributed capacitance that stores energy to be used by the pulser circuit when it delivers a high power transmit pulse to the transducer. In practice, when the transmitter is triggered to generate a high power pulse to the transducer, it also launches a traveling wave as a balanced signal onto the high voltage/ground conductor pair. When the traveling wave reaches the PIM, the PIM supplies the charge needed to replenish what has been drawn from that conductor pair by the transmit pulse. This cable configuration provides all of the required functions, using a four wire interface with all signals transmitted over balanced lines, each terminated with the appropriate characteristic impedance. The balanced, terminated transmission lines provide reduced generation and susceptibility to EMI, low distortion of the transmit waveform, high speed communication, minimal distortion of the amplifier frequency response, and other electrical advantages. In some embodiments, the cable includes an optional shield around the twisted quad to further protect the signal lines from EMI, to reduce electromagnetic interference emitted from the signal lines, and to provide added mechanical integrity.

An alternative cable design according to the present disclosure, offering many of the same advantages described previously in conjunction to the twisted quad configuration, is a shielded, twisted triplet. In this case, two conductors of the twisted triplet serve the multiple functions described previously for the first pair of conductors of the twisted quad. The ground conductor serves as the shield, while the high voltage is carried by the third conductor of the twisted triplet. Since the shield is symmetrical with respect to the conductors of the twisted triplet, there is minimal differential interference signal coupled from the shield to the balanced signal lines that carry the amplifier output. Likewise, by symmetry, there is minimal coupling of interference on the high voltage conductor into the balance signal lines. Furthermore, there is typically very little high frequency noise on the high voltage signal line, except for a brief transient during and immediately after a transmit pulse. Most of that high frequency transient will have dissipated by the time the earliest echo signals of interest return from the vessel tissue. The shielded twisted triplet is a highly manufacturable configuration, with the triplet forming an inherently stable and symmetrical bundle, and with the shield providing mechanical integrity for the cable and protection from external interference.

In the illustrated embodiment, the controller/MEMS hybrid assembly 146 is secured in place relative to the housing 116 by an epoxy 148 or other bonding agent. The epoxy 148 also serves as an acoustic backing material to absorb acoustic reverberations propagating within the housing 116 and as a strain relief for the electrical cable 134 where it is soldered to the controller/MEMS hybrid assembly 146. The pressure transducer 131 electrically communicates with the controller 144 via leads 133 extending therebetween. The controller 144 provides power to the pressure transducer via the leads. Accordingly, the controller 144, disposed at the distal end of the catheter, communicates with both the PMUT MEMS 138 and pressure transducer 131.

The pressure transducer 131 is mounted to measure pressure outside of the imaging core 110, and in a preferred embodiment, is a pressure sensor configured to sense pressure within the vasculature of a patient undergoing treatment. The pressure transducer 131 is electrically connected to the controller 144 which can process, amplify, or condition analog signals from the sensor and transmit corresponding data signals to the proximal end of the catheter.

For this embodiment and other embodiments disclosed herein, the pressure transducer 131 may comprise a rigid housing 135 at least partially surrounding and supporting any type of pressure sensitive transducer. The housing 135 permits the sensor to be sufficiently stress resistant to maintain functionality while embedded within or on the imaging core 110. For example, the pressure transducer 131 may comprise a capacitive sensor, a piezoresistive pressure transducer, a fiber optic pressure sensor such as disclosed in U.S. Pat. Nos. 8,298,156 and 8,485,985 and U.S. Patent Application Publication Nos. 2013/0303914 and 2013/0131523 (each incorporated by reference herein in their entirety), a sensor with a silicon backbone, or any other type of pressure sensor having the requisite durability and stress resistance. In some instances, the pressure transducer 131 includes an array or plurality of sensor elements (e.g., a capacitive pressure sensor array). In some embodiments, the pressure transducer 131 includes a sensor diaphragm assembly. In some embodiments, the sensor diaphragm assembly includes a body having a recess covered by a flexible diaphragm configured to measure fluid pressure. The diaphragm may flex in response to variations in pressure around the diaphragm, thereby reflecting variations in blood pressure, for example. The pressure transducer 131 can then measure and transmit the variations in pressure imparted on the diaphragm assembly.

The sheath 112 includes an open end or apertures that allow the pressure within the sheath to substantially equal the pressure outside the sheath. As such, the pressure measured in the sheath by the pressure transducer 131 is indicative of pressure outside the sheath.

Figure 4:
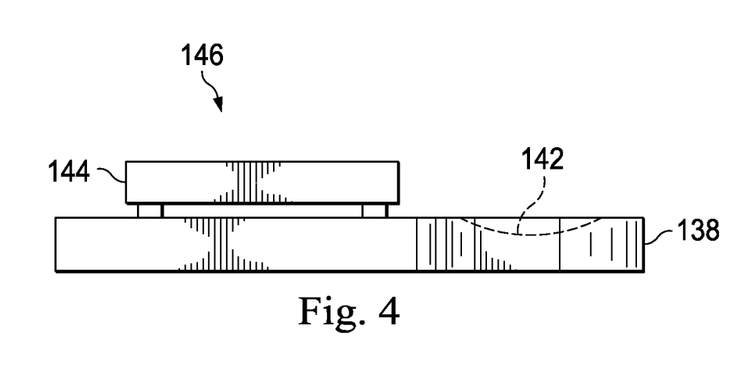
FIG. 4 is a diagrammatic side view of components of the distal portion of the imaging device shown in FIG. 3, including a MEMS component and a controller component, according to an embodiment of the present disclosure.
Figure 5:
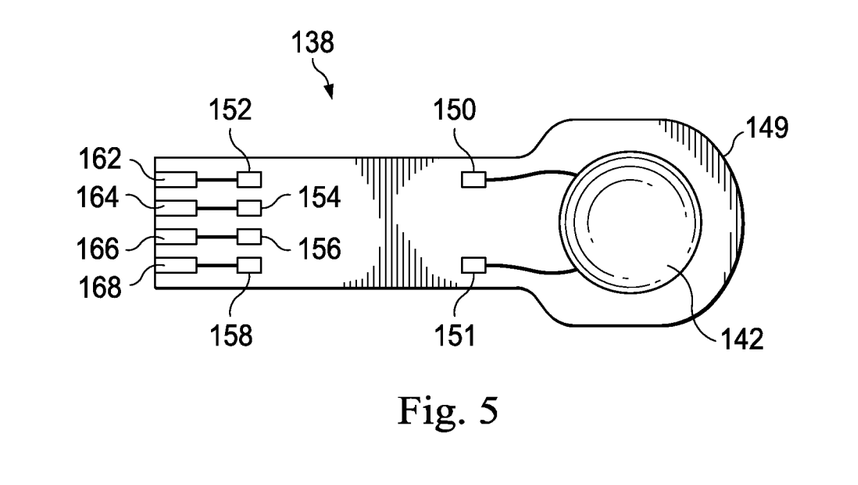
FIG. 5 is a diagrammatic bottom view of the controller component of the components illustrated FIG. 4.
Figure 6:
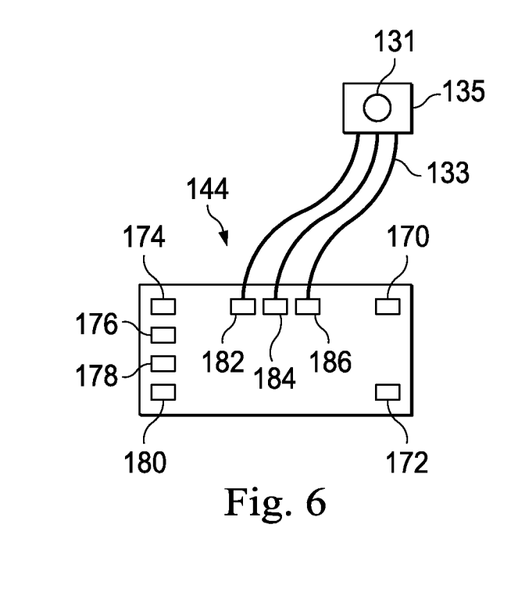
FIG. 6 is a diagrammatic top view of the MEMS component of the components illustrated in FIG. 4.

Referring now to FIGS. 4-6, shown therein are additional aspects of the PMUT MEMS component 138 and controller 144 that form the controller/MEMS hybrid assembly 146. In addition, FIG. 6 shows the pressure transducer 131 attached to the controller 144 via three leads 133 connected to bond pads 182, 184, and 186. The MEMS component 138 in the embodiment of FIGS. 4-6 is a paddle-shaped silicon component with the piezoelectric polymer transducer 142 located in the widened portion 149 of the substrate located at the distal end of the MEMS component 138. The narrow portion of the substrate positioned proximal of the widened portion 149 is where the controller 144 is mounted to the MEMS component 138. In that regard, the MEMS component 138 includes ten bond pads, with bond pads 150, 151, 152, 154, 156, and 158 of the MEMS 138 configured to match up respectively with six bond pads 172, 170, 180, 178, 176, and 174 on the controller 144 (shown in FIG. 6) when the controller is flip-chip mounted onto the MEMS 138. The flip-chip mounting is accomplished using anisotropic conductive adhesive, gold-to-gold thermosonic bonding, and/or other suitable methods. Solder reflow is not convenient for this application in some instances, since the copolymer transducer element is subject to depoling at temperatures as low as 100° C., well below conventional soldering temperatures. Anisotropic conductive adhesive can be cured at temperatures below 100° C., as long as the cure time is increased to account for the low cure temperature. In this embodiment, the bond pads 152, 154, 156, and 158 are coupled to bond pads 162, 164, 166, and 168 by conductive traces included on the MEMS substrate, with the bond pads 162, 164, 166, and 168 serving as terminations for the four conductors of the electrical cable 134, shown in FIG. 3. In that regard, the four conductors of the electrical cable 134 are soldered or otherwise fixedly attached to bond pads 162, 164, 166, and 168, which are electrically coupled with the bond pads 152, 154, 156, and 158. In other embodiments, the four conductors of the electrical cable 134 are soldered or otherwise fixedly attached directly to the controller bond pads 174, 176, 178, and 180. The controller also includes three bond pads 182, 184, and 186 connectable to the pressure transducer 131. Conductive leads extend from the bond pads 182, 184, and 186 to associated bond pads disposed on the pressure transducer 131.

Figure 7:
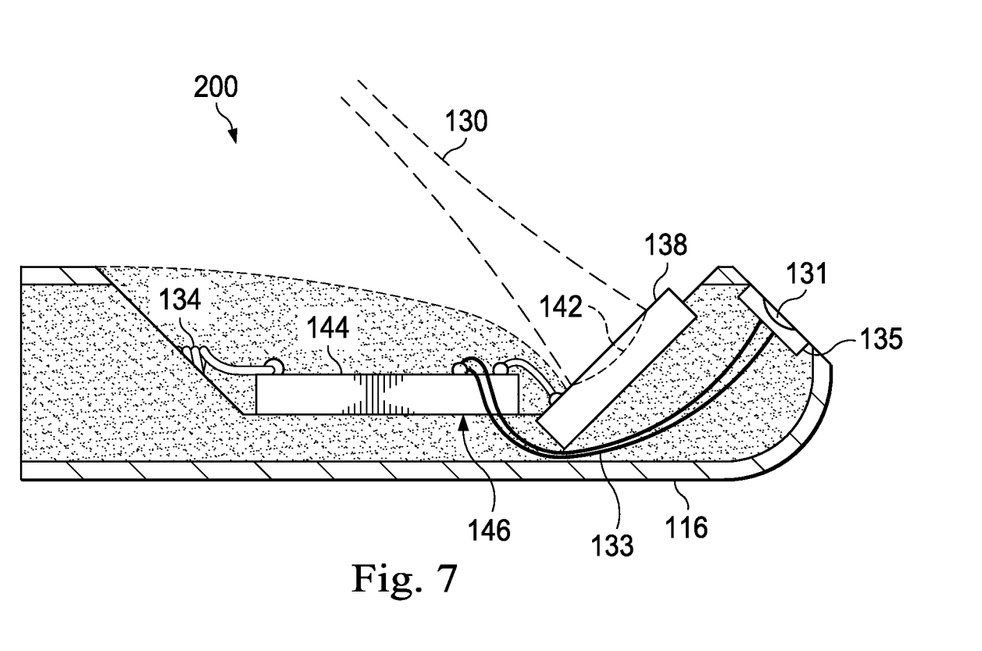
FIG. 7 is a diagrammatic, cross-sectional side view of a distal portion of an imaging device according to another embodiment of the present disclosure.

Referring now to FIG. 7, shown therein is a cross-sectional side view of a distal portion of an imaging core 200 according to another embodiment of the present disclosure. The imaging core 200 may be similar to the imaging core 110 of catheter 102 described above. In that regard, the imaging core 200 includes features and functionality similar to those discussed above with respect to imaging core 110. Accordingly, the same reference numerals have been utilized to refer to analogous features. For example, the imaging core 200 includes a MEMS 138 having a transducer 142, such as an IVUS transducer, formed thereon and a controller 144 electrically coupled to the MEMS 138. However, in the exemplary configuration of FIG. 7, the controller 144 and the MEMS 138 components are wire-bonded together, mounted to the transducer housing 116, and secured in place with epoxy 148 or other bonding agent to form a controller/MEMS hybrid assembly 146. The leads of the cable 134 are soldered or otherwise electrically coupled directly to the controller 144 in this embodiment. The controller 144 includes leads 133 extending to the pressure transducer 131. In some embodiments of this configuration, the MEMS component 138 is a truncated version of the paddle-shaped device shown in FIGS. 4 and 5, with the narrow "handle" portion of the paddle removed. One advantage of the wire-bonding approach is that the MEMS component carrying the transducer 142 can be mounted at an oblique angle with respect to the longitudinal axis of the housing 116 and imaging core 200 such that the ultrasound beam 130 propagates at an oblique angle with respect to a perpendicular to the central longitudinal axis of the imaging core. This tilt angle helps to diminish the sheath echoes that can reverberate in the space between the transducer and the catheter sheath 112, and it also facilitates Doppler color flow imaging as disclosed in U.S. patent application Ser. No. 13/892,108, published as U.S. Patent Application Publication No. 2013/0303907 on Nov. 14, 2013 and U.S. patent application Ser. No. 13/892,062, published as U.S. Patent Application Publication No. 2013/0303920 on Nov. 14, 2013, each of which is hereby incorporated by reference in its entirety.

Figure 8:
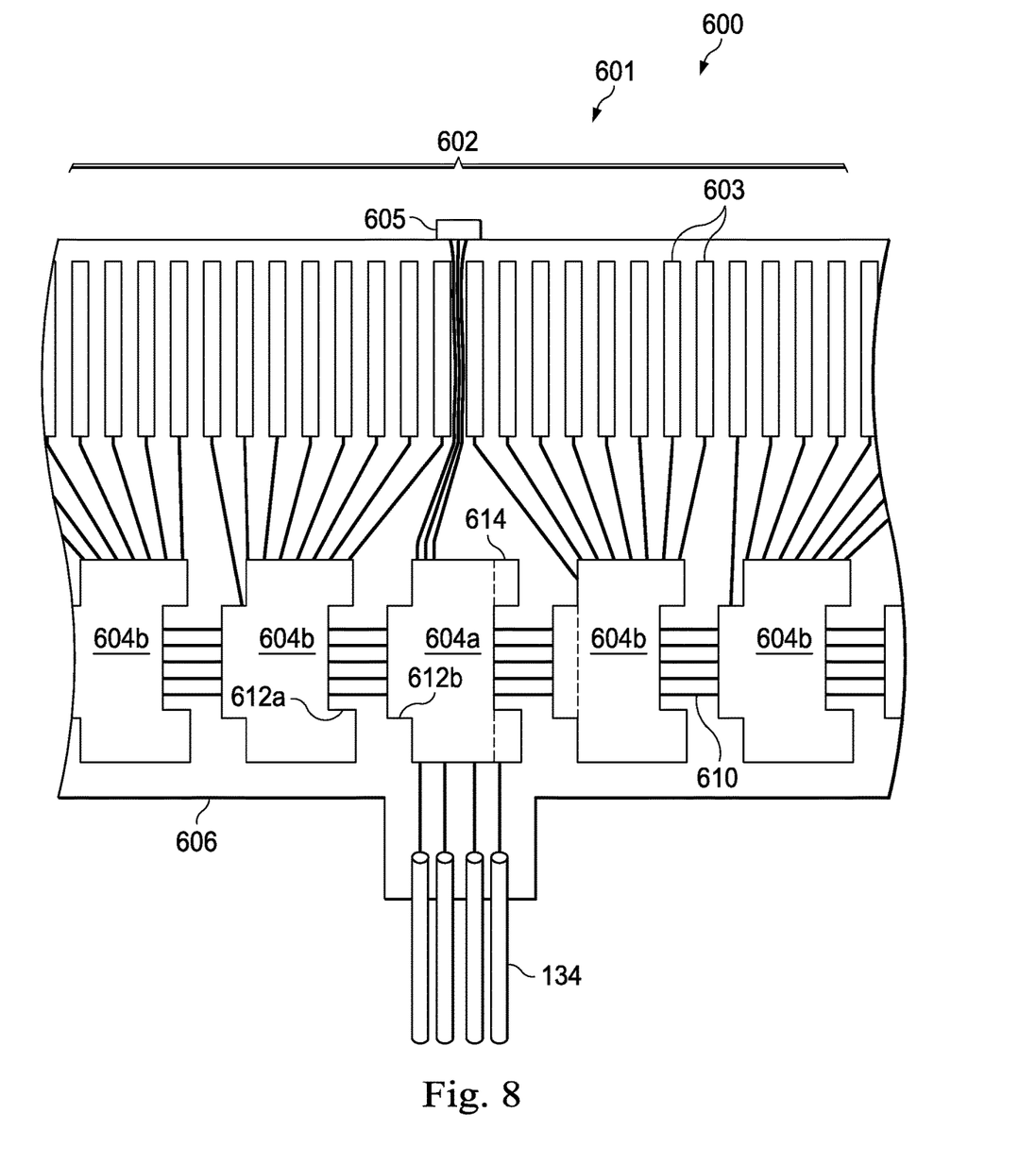
FIG. 8 is a diagrammatic, schematic view of a distal portion of an imaging device according to another embodiment of the present disclosure, with the distal portion being arranged in a flat configuration.

FIG. 8 shows another exemplary embodiment of a portion of an IVUS array and pressure sensing catheter 600. The portion shown may be used at a distal end of an imaging and pressure sensing catheter as described herein. FIG. 8 depicts an ultrasound scanner assembly 601 its flat form. When disposed on a catheter, the assembly 601 is rolled into a cylindrical form. The assembly 601 includes a transducer array 602, transducer control circuits 604 (including controllers 604a and 604b), and a pressure senor 605 attached to a flex circuit 606. The control circuits correspond to the controller described above.

The transducer array 602 includes a plural of ultrasound transducers 603 and replaces the single IVUS transducer described in other embodiments. The transducer array 602 may include any number and type of ultrasound transducers 603, although for clarity only a limited number of ultrasound transducers are illustrated in FIG. 8. In an embodiment, the transducer array 602 includes 64 individual ultrasound transducers 603. In a further embodiment, the transducer array 602 includes 32 ultrasound transducers. Other numbers are both contemplated and provided for. In an embodiment, the ultrasound transducers 603 of the transducer array 602 are piezoelectric micromachined ultrasound transducers (PMUTs) fabricated on a microelectromechanical system (MEMS) substrate using a polymer piezoelectric material, for example as disclosed in U.S. Pat. No. 6,641,540, which is hereby incorporated by reference in its entirety. In alternate embodiments, the transducer array includes piezoelectric zirconate transducers (PZT) transducers such as bulk PZT transducers, capacitive micromachined ultrasound transducers (cMUTs), single crystal piezoelectric materials, other suitable ultrasound transmitters and receivers, and/or combinations thereof.

In some embodiments, the transducer array 602 forms a part of a piezoelectric zirconate transducer (PZT) solid-state IVUS imaging device. In some embodiments, the catheter 600 incorporates capacitive micromachined ultrasonic transducers (CMUTs), and/or piezoelectric micromachined ultrasound transducers (PMUTs). The IVUS imaging and pressure detecting catheter 600 may be associated with the patient interface module (PIM) 104, the IVUS and pressure console or processing system 106, and/or the monitor 108 (FIG. 1).

In the illustrated embodiment, the assembly 601 having 64 ultrasound transducers 603 and at least one pressure sensor 605 includes nine transducer control circuits 604, of which five are shown. Designs incorporating other numbers of transducer control circuits 604 including 8, 9, 16, 17 and more are utilized in other embodiments. In some embodiments, a single controller is designated a master controller and configured to receive signals directly from the electrical cable 134. The remaining controllers are slave controllers. In the depicted embodiment, the master controller 604a does not directly control any of the IVUS transducers 603, but drives the pressure transducer 605. In other embodiments, the master controller 604a drives the same number of IVUS transducers 603 as the slave controllers 604b while driving the pressure transducer 605 or drives a reduced set of transducers 603 as compared to the slave controllers 604b. In the illustrated embodiment, a single master controller 604a and eight slave controllers 604b are provided. Eight transducers are assigned to each slave controller 604b. Such controllers may be referred to as 8-channel controllers based on the number of transducers they are capable of driving.

The master controller 604a generates control signals for the slave controllers 604b based on configuration data and transmit triggers received via the electrical cable 134 and generates control signals for the pressure transducer 605. The master controller 604a also receives echo data from slave controllers 604b and from the pressure transducer 605 and retransmits it on the electrical cable 134. To do so, in some embodiments, the master controller 604a includes an echo amplifier (not shown). In this configuration, the master controller 604a receives unamplified or partially amplified echo data and performs the necessary amplification for driving the echo data along conductors of the electrical cable 134. This may provide additional room for a larger high-fidelity amplifier.

In an embodiment, the flex circuit 606 provides structural support and physically connects the transducer control circuits 604 and the transducers 603 and 605. In an embodiment, the flex circuit 606 further includes conductive traces 610 formed on the film layer. Conductive traces 610 carry signals between the transducer control circuits 604 and the transducers 603 or 605 and provide a set of pads for connecting the conductors of electrical cable 134. Suitable materials for the conductive traces 610 include copper, gold, aluminum, silver, tantalum, nickel, and tin and may be deposited on the flex circuit 606 by processes such as sputtering, plating, and etching. In an embodiment, the flex circuit 606 includes a chromium adhesion layer. The width and thickness of the conductive traces are selected to provide proper conductivity and resilience when the flex circuit 606 is rolled. In that regard, an exemplary range for the thickness of a conductive trace 610 is between 10-50 μm. For example, in an embodiment, 20 μm conductive traces 610 are separated by 20 μm of space. The width of a conductive trace 610 may be further determined by the size of a pad of a device or the width of a wire to be coupled to the trace. Additional details of the flex circuit may be found in U.S. patent application Ser. No. 14/137,269, published as U.S. Patent Application Publication No. 2014/0187960 on Jul. 3, 2014, incorporated herein by reference.

The pressure transducer 605 is disposed in a distal position on the catheter 600 and is disposed at or beyond the top edge of the flex circuit 606 so as to not interfere with operation of the IVUS transducers 603. In this example, the pressure transducer 605 is under control of the master control circuit 604a. Conductive traces, similar to other conductive traces described herein, extend from the master control circuit 604a to the pressure transducer 605. Data or information obtained by the pressure transducer 605 may be communicated to the control circuit 604a, may receive some level of processing, amplification, or other treatment at the control circuit 604a, and may then be communicated on the same electrical conductors of the communication cable 134 as the signals relating to information from the IVUS transducers 603. In one aspect, the control circuit 604a can digitize the one or more of the IVUS or pressure sensor signals prior to transmission.

Figure 9:
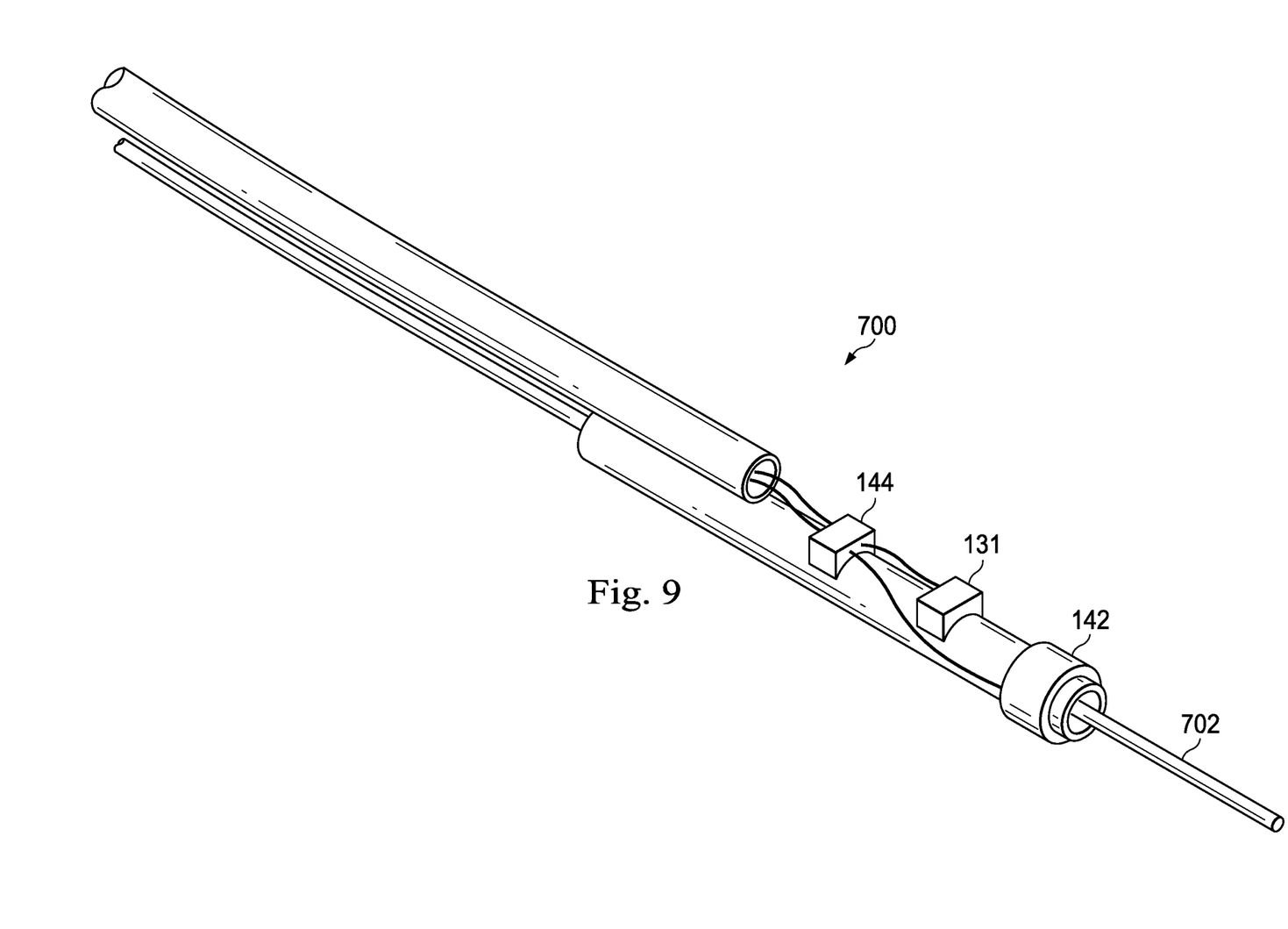
FIG. 9 is a diagrammatic, schematic view of a distal portion of an imaging device according to another embodiment of the present disclosure, with the distal portion being arranged in a flat configuration.

FIG. 9 shows an exemplary catheter as used herein on a monorail pressure sensing catheter 700, where the catheter 700, including the controller 144, the ultrasound transducer array 142, and the pressure sensor(s) 131 are disclosed on or about the catheter, and are advanced to a patient's target region over a guidewire 702.

As the circuit may be rolled to form the finished scanner assembly, the control circuits 604, including both master and slave controllers, may be shaped accordingly. This may include a control circuit 604 edge configured to interface with an edge of an adjacent control circuit 604. In some embodiments, the control circuits 604 include interlocking teeth 612a and 612b. For example, control circuits 604 may be formed with a recess and projection 612a that interlocks with a recess and projection 612b of an adjacent control circuit 604 to form a box joint or finger joint. In some embodiments, a control circuit 604 includes a chamfered edge 614, either alone or in combination with a recess and projection. The chamfered edge 614 may be configured to abut an edge of an adjacent control circuit 604. In some such embodiments, the edge of the adjacent controller is chamfered as well. In some embodiments, each of the controllers 604 interlocks with two adjacent controllers utilizing a similar recess and projection interface. Other combinations, including embodiments utilizing a number of different mechanisms, are contemplated and provided for. For example, in an embodiment, edges of slave control circuits interfacing with a master control circuit have a recess and projection configuration with a chamfered region while edges of slave control circuits interfacing with other slave control circuits have a recess and projection configuration without a chamfered region. Edge configurations that interlock adjacent control circuits 604 may allow for closer control circuit spacing 604 and a reduced diameter in the rolled configuration. Such configurations may also interlock to create a rigid structure and thereby provide additional structural support for the rolled scanner assembly.

An exemplary method of using the device disclosed herein is inferred by all the teachings herein as would be apparent to one of ordinary skill in the art and explicitly disclosed in the following paragraphs. The catheter is advanced through the vessel toward a target region or area of interest in the patient. This may be a target area forming a part of the patient's vasculature, but may also be other parts of the patient's body. In some embodiments, the catheter is advanced over a guidewire, such as the guidewire 702 in FIG. 9.

With the catheter in the target region, the IVUS transducer and the pressure transducer sensors may be activated to obtain information relating to the target region. In some embodiments, this may be used to obtain information relating to stenosis in a vessel. The IVUS transducer may be used to image the target region of the patient, and the pressure transducer may be used to measure pressure within the vessel. This may occur simultaneously or at separate times depending on the arrangement of the system. Signals representing the ultrasound imaging and the pressure are communicated from the transducers to the controller or ASIC. The pressure or flow information may be transmitted via the same electrical cable, and may be communicated via the same conductor from the controller to the PIM and ultimately to the console 106, which may be presented on the display 108 to the clinician. In some embodiments, the information representing the ultrasound imaging and the pressure are communicated from the controller to the PIM in real time. In other instances, the information is stored on the controller and then sent later.

With both ultrasound transducers and pressure transducers on the same catheter, the systems, devices, and methods herein are capable of carrying out both imaging and pressure sensing. In one example, the combination catheter may be used to perform an IVUS pullback to image the vessel and, either during the pullback or at a separate time interval, may be used to sense pressure in the vessel. Accordingly, using a single catheter, medical personnel may be able to receive more information relating to a patient's condition than could otherwise be obtained. In addition, since the signal from the ultrasound transducers and pressure transducers are communicated along the catheter using shared conductors and other electrical components, such as the same conductors in the communication cable 134, the catheter may be maintained at a size small and effective for assessing even small vessels of the vasculature. Because of the additional information that may be obtained from a single catheter, medical personnel may more efficiently assess a patient. In some instances, this reduction in assessment time may also result in reduced time to actual treatment, reducing costs to the patient. In addition, due to the shared components, the overall diameter of the catheter may be smaller than could otherwise be achieved. In addition, some manufacturing steps may be eliminated when compared to manufacturing with distinct IVUS imaging and pressure transducers.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intravascular ultrasound (IVUS) device, comprising:
   a flexible elongate member comprising a proximal portion and a distal portion configured to be positioned within a vessel of a patient;
   a substrate coupled to the distal portion of the flexible elongate member and comprising a plurality of conductive segments;
   a controller mounted on the substrate;
   an ultrasound transducer array mounted on the substrate and in communication with the controller, wherein the ultrasound transducer array comprises a plurality of ultrasound transducers;
   a pressure sensor mounted on the substrate distal of the ultrasound transducer array, wherein the pressure sensor is in communication with the controller via the plurality of conductive segments, and wherein a portion of each of the plurality of conductive segments is positioned between two ultrasound transducers of the plurality of ultrasound transducers; and
   a plurality of wires extending from the distal portion of the flexible elongate member to the proximal portion of the flexible elongate member, wherein a distal end of the plurality of wires is connected to electrical contacts positioned on a proximal region of the substrate, wherein both the ultrasound transducer array and the pressure sensor are in electrical communication with the plurality of wires such that the plurality of wires is configured to carry both signals representing information captured by the ultrasound transducer array and information captured by the pressure sensor.

2. The device of claim 1, wherein the controller is configured to communicate the signals based on information from both the ultrasound transducer and the pressure sensor on the plurality of wires.

3. The device of claim 2, wherein the pressure sensor connects to the controller via three leads.

4. The device of claim 1, wherein a proximal portion of the plurality of wires is coupled to a connector configured to connect the plurality of wires to a patient interface module (PIM).

5. The device of claim 1, wherein the controller is disposed adjacent the ultrasound transducer array.

6. The device of claim 1, wherein the flexible elongate member comprises a guidewire lumen for receiving a guidewire.

7. The device of claim 1, further comprising a plurality of slave controllers coupled to the distal portion of the flexible elongate member and in communication with the controller, wherein the ultrasound transducer array is in communication with the controller via the plurality of slave controllers, and wherein the pressure sensor is in direct communication with the controller.

8. The device of claim 7, wherein the controller is configured to:
   directly control operation of the pressure sensor; and only indirectly control, via the plurality of slave controllers, operation of the ultrasound transducer array.

9. The device of claim 1, wherein the substrate comprises a flex circuit, wherein the pressure sensor is mounted to a distal end of the flex circuit, and wherein the plurality of conductive segments is formed in the flex circuit.

10. The device of claim 9, wherein the flex circuit is positioned around the distal portion of the flexible elongate member such that the ultrasound transducer array encircles the distal portion of the flexible elongate member.

11. The device of claim 1, wherein the pressure sensor comprises a pressure transducer.

12. The device of claim 1, wherein the plurality of wires comprises only three wires or only four wires, wherein all of the plurality of wires are in a twisted configuration, and wherein both the ultrasound transducer array and the pressure sensor are in electrical communication with a wire pair of the plurality of wires such that the wire pair the plurality of wires is configured to carry both signals representing the information captured by the ultrasound transducer array and the information captured by the pressure sensor.

13. An intravascular ultrasound (IVUS) imaging and pressure sensing system, comprising:
a catheter configured to be positioned within a vessel of a patient, the catheter comprising:
a flexible elongate member comprising a proximal portion and a distal portion;
a substrate coupled to the distal portion of the flexible elongate member and comprising a plurality of conductive segments;
a controller mounted on the substrate;
an ultrasound transducer array mounted on the substrate and in communication with the controller, wherein the ultrasound transducer array comprises a plurality of ultrasound transducers;
a pressure sensor mounted on the substrate distal of the ultrasound transducer array, wherein the pressure sensor is in communication with the controller via the plurality of conductive segments, and wherein a portion of each of the plurality of conductive segments is positioned between two ultrasound transducers of the plurality of ultrasound transducers; and
a plurality of wires extending from the distal portion of the flexible elongate member toward the proximal portion of the flexible elongate member, wherein a distal end of the plurality of wires is connected to electrical contacts positioned on a proximal region of the substrate, wherein both the ultrasound transducer array and the pressure sensor are in electrical communication with the plurality of wires such that the plurality of wires is configured to carry signals representing both information captured by the ultrasound transducer array and information captured by the pressure sensor; and
a user interface in communication with the catheter and configured to present information based on the signals carried by the plurality of wires.

14. The system of claim 13, wherein the controller is configured to communicate the signals based on information from both the ultrasound transducer array and the pressure sensor on the plurality of wires.

15. The system of claim 14, wherein the pressure sensor connects to the controller via three leads.

16. The system of claim 13, wherein a proximal portion of the plurality of wires is coupled to a connector configured to connect the plurality of wires to a patient interface module (PIM).

17. A method of assessing a patient comprising:
receiving information captured by an ultrasound transducer array mounted on a substrate, wherein the ultrasound transducer array comprises a plurality of ultrasound transducers, wherein the substrate is coupled to a distal portion of a catheter positioned within a vessel of a patient and comprises a plurality of conductive segments;
receiving information captured by a pressure sensor mounted on the substrate distal of the ultrasound transducer array;
generating communication signals representing the information from the ultrasound transducer array and the information from the pressure sensor at a controller mounted on the substrate, wherein the pressure sensor is in communication with the controller via the plurality of conductive segments, wherein a portion of each of the plurality of conductive segments is positioned between two ultrasound transducers of the plurality of ultrasound transducers; and
transmitting, over a plurality of wires extending from the controller to a proximal portion of the catheter, the communication signals representing both the information captured by the ultrasound transducer array and information captured by the pressure sensor from the controller to a user interface, wherein a distal end of the plurality of wires is connected to electrical contacts positioned on a proximal region of the substrate.

18. The method of claim 17, wherein the receiving the information captured by the ultrasound transducer array and the receiving the information captured by the pressure sensor are performed simultaneously.

19. The method of claim 17, wherein the transmitting the communication signals representing both the information captured by the ultrasound transducer array and the information captured by the pressure sensor comprises transmitting signals in real time as the information captured by the ultrasound transducer array and the information captured by the pressure sensor is received from the ultrasound transducer array and the pressure sensor.

20. The method of claim 17, wherein the generating includes converting analog signals received from at least one of the pressure sensor or ultrasound transducer array into digital signals prior to the transmitting.

* * * * *